United States Patent [19]

Hup et al.

[11] 4,053,642
[45] Oct. 11, 1977

[54] STARTER CULTURE PRODUCTION

[75] Inventors: Gerhard Hup, Ede; Jacobus Josephus Stadhouders, Bennekom, both of Netherlands

[73] Assignee: Stichting Bedrijven Van Het Nederlands Instituut voor Zuivelonderzoek, Ede, Netherlands

[21] Appl. No.: 586,363

[22] Filed: June 12, 1975

Related U.S. Application Data

[63] Continuation-in-part of Ser. No. 356,179, May 1, 1973, abandoned.

[30] Foreign Application Priority Data

May 2, 1972 Netherlands .......................... 7205909

[51] Int. Cl.² .......................... A23C 9/12; A23C 19/02; A23C 21/00
[52] U.S. Cl. .......................... 426/36; 195/96; 195/100; 426/41; 426/43; 426/61; 426/522
[58] Field of Search .......................... 426/34, 36, 41, 43, 426/61, 583, 522; 195/96, 100

[56] References Cited

U.S. PATENT DOCUMENTS

| | | | |
|---|---|---|---|
| 3,048,490 | 8/1962 | Lundstedt | 426/43 X |
| 3,354,049 | 11/1967 | Christensen | 195/100 |
| 3,420,742 | 1/1969 | Farr | 426/61 |
| 3,708,307 | 1/1973 | Lundstedt | 426/583 X |
| 3,968,256 | 7/1976 | Sing | 426/36 X |

OTHER PUBLICATIONS

Lundstedt, E., Citrated Whey Starters, J. Dairy Sci., vol. 45, 1962 (pp. 1320–1326).
Webb et al., By-products From Milk, The Avi. Publ. Co. Inc., Westport, Conn., 1970, (pp. 43–45).

*Primary Examiner*—David M. Naff
*Attorney, Agent, or Firm*—Fleit & Jacobson

[57] ABSTRACT

Bacteria cultures for use as an inoculant in the preparation of starters and fermented milk products are produced by culturing a milk sugar fermenting bacteria on a culture medium containing whey, a non-whey protein in an amount of about 0.1 to 0.5 weight percent and a buffer mixture. After culturing, the bacteria may be concentrated and freeze dried to produce a starter culture concentrate which can be added directly to cheese milk. When preparing the culture medium, the whey and non-whey protein are pasteurized separately.

14 Claims, 3 Drawing Figures

STARTER CULTURE PRODUCTION

This is a continuation-in-part application of Ser. No. 356,179, filed May 1, 1973, now abandoned.

The present invention relates to a method of producing a composition for use an an inoculant material in the preparation of starters and fermented milk products.

In the preparation of cheese, the milk casein is made insoluble, and subsequently it is separated together with the milkfat from the major portion of the aqueous phase (whey). This insolubilization is achieved by the action of a curdling enzyme and/or by lowering the pH value of the aqueous phase. The pH value may be lowered by adding an acid or acid forming materials, but mostly it is effected by the action of a starter.

A starter is a culture of one (pure culture) or more (mixed culture) strains of bacteria which are capable of reacting milk sugar into lactic acid. In the Netherlands a mixed culture is usually employed.

Such a starter is added in a small quantity, in the order of 1% of the volume of the milk, to the cheese milk and therein the starter bacteria will begin to multiply. This process promotes the desired conditions for curdling of the milk and/or for the subsequent exudation of the whey from the curd during its treatment — both actions taking place under the influence of the lowering of the pH value as a result of the production of lactic acid — and the desired degree of ripeness of the cheese as the result of the action of the produced enzymes.

According to one of the usual methods, a starter is prepared by inoculation of a small quantity of the desired bacteria into a proper medium and incubating it.

In general, the medium employed is highly pasteurised skim milk and the incubating temperature is approximately 20° C. As already stated, the pH value of the medium is lowered following the production of lactic acid. Moreover, other changes take place in the medium (other reaction products are formed). This altogether causes a decrease of the growth rate. Preferably, the starter is used immediately after its preparation or it must be cooled and stored at a low temperature, as otherwise the activity is reduced, which means that the rate of acid production by the bacteria during the preparation of the cheese is reduced.

The cultivation of starters in a cheese factory presents objections in matters of extra work, non-reproducible properties and even failures. Therefore it has been suggested to cultivate the bacteria cultures required for cheese preparation is specialised centres. These starters are then distributed in a frozen form, either after concentration or not, and sometimes even in a dried form. The drying can be achieved by evaporating the water in a stream of hot air, or by sublimating ice at a very low temperature under reduced pressure. Generally, the lactic acid formed is neutralized before drying the bacteria culture, but if desired, this may be done during the incubation. This neutralisation is most important since, otherwise, in the concentrating step the lactic acid content might become too high. Furthermore, the starter, after specific additions have been made can be subjected to certain treatments, first in a centrifuge, for example a bactofuge, wherein it is divided into a portion that contains substantially all bacteria cells and a relatively cell free portion, of which portions only the first one needs to be frozen. Such frozen cell concentrates are, without one or more subsequent inoculations, proper to be used in the preparation of a starter or to be added to the cheese milk directly instead of the starter. Consequently, as other possible forms in which the starter may be delivered must be inoculated at least once to obtain a starter having a satisfying activity, by using frozen cell-concentrates an important saving in manufacturing costs is achieved. However, on the other hand such cultures do not contribute substantially to cheese making yields, whereas starters that have not been separated in a centrifuge, so so effectively. It is for this reason that the frozen starter concentrates may not be too expensive.

It is obvious that skim-milk may be employed as a culture medium at a centralised starter preparation, just as is the case in cheese-making plants. This has a disadvantage inasmuch as in the concentrate, or in the dried starter powder also, milk protein is accumulated, so that finally the number of bacteria per gram will not be sufficiently high. The required volume of the product will be increased, so that all sorts of problems will arise such as storage and transport difficulties, which cause an increase of the costs. This can be avoided by dissolving the milk protein before the concentrating step by neutralisation with sodium hydroxide and by adding e.g. sodium citrate. This method is expensive since in that case the protein is not transferred into the cheese, but an advantage is that in this manner the concentration may be performed by means of a centrifuge. In another, but equally expensive manner N. J. Berridge and P. Wilson (18 Int. Dairy Congr. (1970) 1E 276) achieved a corresponding improvement by a preceding hydrolysis of the protein by means of pepsin. Hydrolysis by trypsin and papain is also mentioned.

Moreover it is possible to use culture media ("synthetic media") containing in addition to a source of carbon — for example glucose — and salts, also yeast extract, corn steep liquor, or similar materials as growth promoting materials. Such stimulants may also be added to whey and even to skim-milk. However, such mixtures have the disadvantage that they can cause changes in the microbial composition of the culture, because stimulants promote growth of certain bacteria (variants) at the expense of others. In mono-cultures these may be slowly growing variants; in mixed cultures there may occur changes in the ratio of the numbers of the various species and strains originally present. Besides this, and despite the presence of stimulants, growth in such media is often poor whilst they are relatively expensive.

In this matter, it has also been proposed to use media consisting predominantly of whey. However, without supplementing additional nitrogen sources, an insufficient amount of nitrogen can be assimilated from said media.

J. M. Lattey (N.Z.J. Dairy Sci 3, (1968) 35) found that the slow development of starters in whey was improved by the addition of yeast extract. In Dutch Pat. Application No. 70.05485, the equivalent of U.S. Patent application Ser. No. 818,417 of Apr. 22, 1969 (Miles Laboratories Inc.), it is proposed to use a medium prepared by dissolving whey and milk powder in water, treating it with protease, and adding corn steep liquor.

It was proposed by E. G. Pont and G. L. Holloway (Austral. J. Dairy Technol. 23, (1968), 22) to use whey to which yeast extract and trypton have been added. In such a medium, sodium lactate acts as a limiting factor for the growth of bacteria.

However, such media also contain substances which, through stimulation of the growth of certain bacteria in mixed cultures, can lead to changes in the desired ratios and thus to deviating starters. However, this problem is not met in mono-cultures, to which the abovementioned publications relate.

In order to obtain large numbers of bacteria per liter, the lactic acid formed during cultivation is often neutralized (as see Dutch Patent Application No. 70.05485, the equivalent of U.S. Patent Application No. 818,417 of Apr. 22, 1969). The disadvantages of this system are a.o. an increased probability of the development of homologeous bacteriophages, and possibly changes in the ratio between the various bacteria. Furthermore, undesirable salts may be formed on neutralisation.

It was found that the disadvantages of known methods can be eliminated by using a culture medium prepared by cultivating a culture of at least one strain of milk sugar fermenting bacteria in a culture medium including (1) whey, such as diluted whey, whey having a low lactose content, and aqueous dispersions of whey powder (2) an aqueous dispersion of non-whey protein selected from the group consisting of soya protein and milk protein in such an amount that the culture medium contains about 0.1 to 0.5 weight percent preferably about 0.13 to 0.26 weight percent, of non-whey protein, and (3) a buffer mixture, said whey, and said aqueous dispersion not being pasteurized together. Preferably, the whey, the aqueous dispersion of non-whey protein and the buffer mixture are each pasteurized separately.

This method makes it possible to obtain a concentrated culture of lactic acid bacteria which, just as in the usual bulk starters, can be introduced directly into the cheese milk without previous cultivation. Furthermore, it is a particular advantage that the ratio of the numbers of various strains and variants of bacteria present in the culture according to the present invention is the same as in the normal bulk starters, whilst the activity has a sufficiently high value for cheese manufacture. Furthermore, and as opposed to cultures obtained according to known methods, the cost of the present culture medium is low and the final number of bacteria per weight unit is high.

If the carbohydrate contents of the medium to be used are too low, this may be supplemented e.g., by lactose, glucose or another assimilable carbohydrate (Vide S. Orla-Hensen, The Lactice acid bacteria, Copenhagen, 1919; and: idem, Erganzungsband, Copenhagen, 1943).

The use of demineralized whey does not fall within the scope of the present invention.

Preferably whey heated for 10 to 30 minutes at a temperature of 85° C to 100° C is used as a whey based solution. It is efficient to clarify the whey by centrifuging after heating.

For the prevention of changes in the usual composition eventually occurring in a whey-based solution, an aqueous colloidal dispersion of soya protein and/or milk protein is used. Only a small quantity of this solution is needed. Preferably 5% to 10% by volume of skim-milk, or a corresponding quantity of an aqueous dispersion of skim-milk powder is used.

The buffer mixture used according to the present invention prevents an early inhibition of the growth of bacteria, which would be the result of too low a capacity of the culture medium without the use of said buffer mixture, which serves to prevent a drop in the pH following the production of lactic acid.

Various known substances may be used as a buffer mixture so long as they exercise no damaging influence on the bacteria, and so long as they, from a toxicological standpoint, are acceptable to be used in food.

Preferably, the buffer mixture is used in the form of an aqueous solution. The alkali metal salts of orthophosphoric acid such as, for example, an aqueous solution of equi-molar quantities of disodium-hydrogenphosphate and potassium-dihydrogenphosphate are very suitable agents.

The addition of phosphates to milk-free culture media was suggested in Dutch Patent Application No. 66.05337, the equivalent of U.S. Patent application Ser. No. 451,311 of Apr. 27, 1965 (page 4, lines 29 a.ff.) because these compounds, in a concentration of up to 0.1% by weight, would promote the formation of high concentrations of cells.

However, according to the present invention, a mixture of phosphates is used as a buffer in order to retard a drop in the pH value following the production of lactic acid. Evidently, then, the required quantity is greater. A ten-fold higher concentration than proposed in the last mentioned Dutch Patent Application is efficiently used.

To prevent a flocculation of protein, which may reduce the starter activity, the components of the culture medium may not be pasteurised after having been brought together for inoculation with the bacteria.

The pasteurization is usually carried out by heating at a temperature of 100° C for a period of 30 minutes ("steaming"). If use is made of cheese whey, heated to 75° C to eliminate rennet and starter activity, and subsequently cooled and centrifuged and if this liquid is "steamed", contingently after the previous addition of a phosphate mixture or skim-milk (or another protein dispersion) or both, then a coagulation of protein occurs, which is thus no longer available for assimilation. This results in a lower starter activity after the starter bacteria have been cultivated therein. If the same process is carried out after having precedingly digested the whey proteins partially by means of trypsin, then, indeed, after "steaming" no protein sediment will be present; but this method, again, is expensive.

However, a satisfactory result is obtained by first "steaming" and subsequently centrifuging the whey. After cooling to a lower temperature, the treated whey is mixed with the buffer mixture and the already separately "steamed" skim-milk.

If the buffer mixture is used as an aqueous solution it should, preferably be pasteurized as well. The mixing occurs in such a manner that the mixture obtained preferably has a temperature not exceeding 65° C. Otherwise, undesirable precipitates might be formed, though this is not always the case.

Using this separate pasteurization, no co-precipitate of whey and milk protein will be formed, and the activity of the starter is normal when 5% skimmilk is used. Steaming of rennet whey is not absolutely necessary. If rennet whey is acidified with hydrochloric acid to a pH of 6.0 thereafter heated for 10 minutes at a temperature of 85° C, and subsequently centrifuged before phosphates and skimmilk are added, then the starter, even after addition of as little as 5% of skimmilk, has a substantially normal activity.

If the bacteria after inoculation into the culture medium are incubated sufficiently long they can then be separated from the aqueous phase, for example, by means of freeze drying or by means of a bactofuge such that, whether or not, the pH of the medium has initially been increased to a more neutral value and the small, but still present, quantity of milk protein, can be prevented from being thrown out together with the bacteria, by dissolving the protein by means of sodium citrate or a protein dissolving agent. If the protein is not dissolved previously, a bactofuge may be stopped up very quickly.

Therefore, if skimmilk is used as a culture medium it is always neutralised and, subsequently, its casein is dissolved ("clarified") by means of the addition of 1% sodium citrate. On centrifuging a culture in skimmilk and a culture according to the invention, there is obtained in both cases a quantity of sediment of the same order of magnitude if both are first neutralised to a pH of 6.6 and then clarified with a solution of sodium citrate.

With the aid of a bactofuge it is possible, while employing the method according to the present invention, to concentrate more than 90% of the bacteria of a culture according to the present invention, into a volume that is 2% of that of the original culture, and thereby, the concentrate is obtained in a continuous stream and can be processed without any previous resuspension being necessary.

The said obtained bacteria concentrate can, in a known manner, be brought into a form suitable for storage and transport, for example, by rapidly freezing it to a temperature of $-40°$ C, preferably after the addition of lactose, and further storing it at a temperature of preferably not above $-10°$ C. The concentrated bacteria culture may also be lyophilized. The bacteria concentrate thus obtained, according to the present invention, can simply be introduced into the cheese-making milk, and exhibits therein a good activity. Thus, cheese can be prepared from milk which has been coagulated by the addition of rennin and said bacteria concentrate as the starter, the coagulated milk cut into small pieces, the resulting mixture gently stirred and, if necessary, heated to promote exudation of whey, and whey drained off, and the curd collected and shaped in a mold.

The bacteria concentrate obtained can also, without previous incubation, be directly introduced into cream to be fermented for the preparation of butter. Other fermented-milk products such as yoghurt and buttermilk, for example, can be obtained in a similar manner though, as will be self evident, the composition of the bacteria concentrate must be adapted to the purpose for which it is to be used. Thus, such fermented milk products can be prepared from milk which has been inoculated with the aforesaid bacteria concentrate as the starter comprising a culture of microorganisms and the temperature of the inoculated milk is adjusted to obtain the necessary growth of the microorganisms.

Various data concerning the composition of the culture medium, its behaviour on heating, and the activity of the obtained starter are given in the following Table A. Concerning the activity, it may be stated that, with the object of obtaining an impression of the usefulness of a starter for cheese-making, its total number of germs per milliliter is often determined. However, a better impression is obtained by measurement of the rate of acid production under strictly determined circumstances in the so called activity determination. To this end, 1% of the starter is introduced into the cheese milk. The milk is thereafter maintained for 6 hours at a temperature of 30° C, and following this acidity value is determined by titration with 0.1 N solution of NaOH, phenolphthalein being employed as an indicator (Dutch Standards Method NEN 913). The activity is expressed as °N, this being the number of milliliters 0,1 N NaOH used per 100 milliliters of incubated mixture. This activity is mentioned in the table.

TABLE A

| Test number | Basic liquid | pH lowered to | thereafter heated during 10 min 75°C | 10 min 85°C | 30 min 90°C | 30 min 100°C | centri-fuged | pH increased to | treated with 0.04% trypsine (BDH) and centri-fuged | heated for 30 mins at 100°C | subsequently added (vol. %) skim milk | phosphate solution 1) | heated for 30 mins at 100°C | Result: precipitate present before inoculation 2) | activity according to NEN 913° N |
|---|---|---|---|---|---|---|---|---|---|---|---|---|---|---|---|
| 1 | skimmilk | | | | | | | | | | | | | | 62 |
| 2a | whey | | + | | | | + | | | | | | | – | 48 |
| B | whey | | + | | | | + | | yes | | | | | + | 41 |
| C | whey | | + | | | | + | | yes | | 10 | 1 | ++ | + | 61 |
| d | whey | | + | | | | + | | yes | + | 10 | 1 | ++ | – | 63 |
| 3a | whey | | + | | | | + | | yes | | 10 | 1 | ++ | – | 35 |
| b | whey | | | | | +++ | + | | | | | | | +++ | 33 |
| c | whey | | | | | +++ | + | | | | 10 | 1 | ++ | +++ | 36 |
| 4a | whey | | | | | | + | | | | 2½ | 1 | | – | 32 |
| b | whey | | | | | | + | | | | 5 | 1 | | – | 55 |
| c | whey | | | | | | + | | | | 10 | 1 | | – | 58 |
| d | whey | | | + | | | + | | | | 5 | 1 | | – | 63 |
| 5 | whey | 6,0 | | | | | + | 6,8 | | | | | | – | 58 |
| 6 | whey | 4,6 | | | | | + | 6,8 | | | | | | – | 60 |

1) Phosphate solution comprises per 100 ml 28.3 g Na2HPO4 . 2H2O and 21.6 KH2PO4
2) – No precipitate present.
+ formed in small quantities.
+++ much precipitate present.

The invention will be better understood from the following examples.

EXAMPLE I

Figure 1:
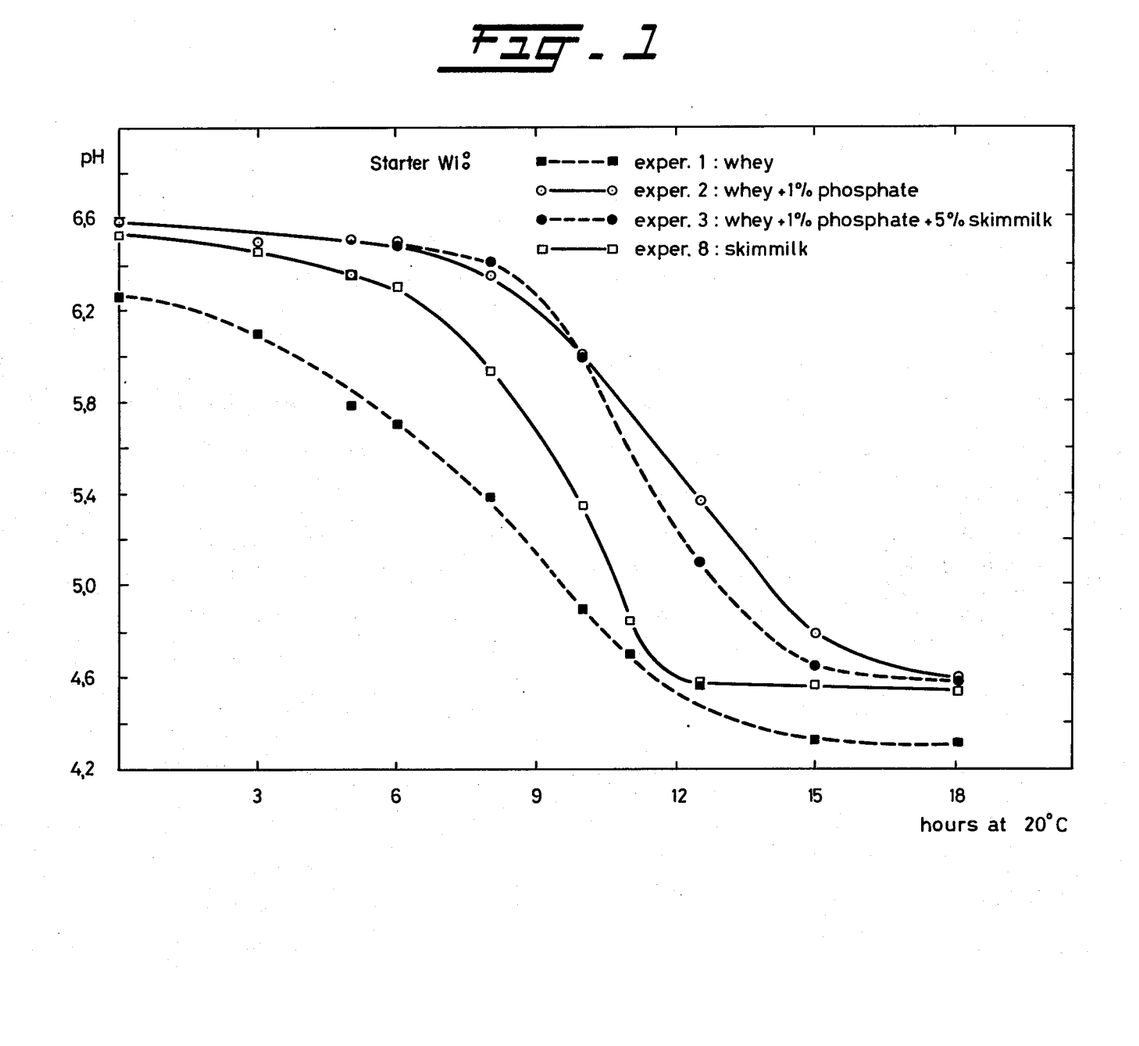
Figure 2:
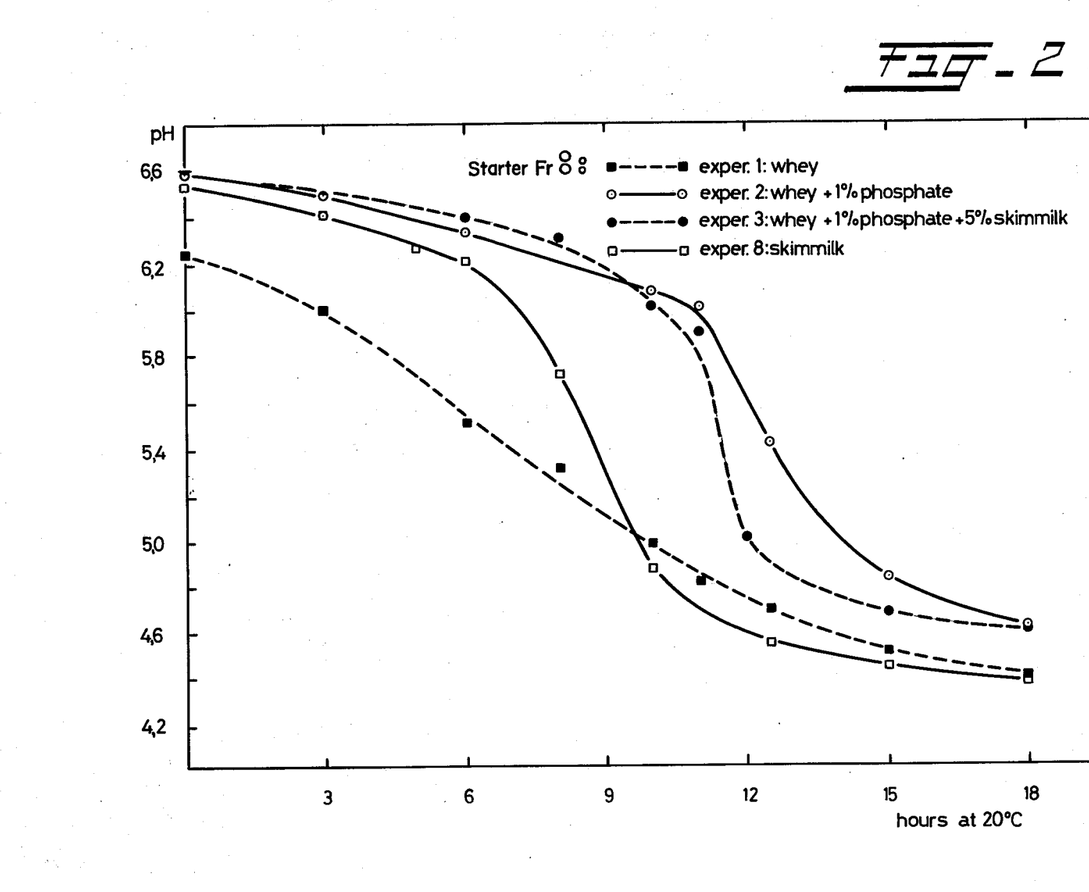

A mixture obtained at cheese-making from the first and the second whey drainages, which by centrifuging had already been freed as well as possible of fat and curdfines, was pasteurized for 10 minutes at 90° C during which time a major part of the protein was precipitated. The precipitate was removed by centrifuging for 10 minutes at 10.000 × g. Together with the pre-treated whey, other pasteurized liquids, such as those given in table B, were introduced into sterile flasks of 100 ml to form culture media which were inoculated with 1% of one of the starters Wi or Fr8. Subsequently the medium was incubated for 21 hours at 20° C. Thereafter the activity of the starters obtained was determined in milk re-constituted from powder of low-heat skimmilk (L-milk) as well as in skimmilk which was heated at 115° C for 10 minutes (H-milk). The results are stated in Table B. It appears that in trials 3 and 5 the activity of the starter was substantially as good as the activity of a starter cultivated in the usual way in skimmilk (trial 8); whilst in trials 6 and 7, in which the concentration of the nutrients was reduced due to the addition of water, the activity appeared to be lower. In separately inoculated culture media, in some cases the reduction of the pH value during the period of incubation was determined. The results are given in the accompanying FIGS. 1 and 2. Due to the buffering capacity of the introduced phosphate mixture, the lowering of the pH initially was slower than in skimmilk, but at continued incubation it appeared that the lowering of the pH occurred as in a normal skimmilk culture.

tor and therein, under stirring, cooled to a temperature of 40° C and subsequently brought up to a pH of 6.8 by adding a solution of NaOH. Thereafter 120 liters of skimmilk and an aqueous solution of 14 kg of $Na_2HPO_4.2H_2O$ and 11 kg of $KH_2PO_4$ in 25 kg of water both having been heated to a temperature of 90° C, were added. The tank contents were then cooled to 20° C and inoculated with 1% of the starter Wi, which starter was obtained from a frozen inoculated starter culture. This is milk inoculated with bacteria, not incubated but immediately stored at freezing temperatures and before use, thawed, incubated and subsequently twice subcultured.

After 18 hours incubation, the contents of the incubator were brought to a pH of 6.9 with NaOH, whilst sodium citrate to at a weight of 5 kg dissolved in 8 liters of water was introduced to dissolve the protein therein. The clarified starter was then centrifuged in a bactofuge and the sludge was pumped through a cooler to a tank, in which it was stored at a temperature of approximately 2° C. A quantity of 45 liters of sludge was obtained into which a solution of 3.5 kg lactose in 4 liters of water was introduced. Approximately 300 g of this liquid was introduced into each of a number of cans, which were then passed through a freezing tunnel to freeze their contents at a temperature of −35° C and then stored at a temperature of −40° C.

After a day of storage at −40° C, the total number of germs of the deep frozen starter concentrate and its activity were determined. After 5 days of storage at −40° C the total number was determined again to compare it with that of the Wi starter prepared according to the usual methods. Moreover, the total number and the number of aroma bacteria were determined in respec-

Table B

| | Test | | | | | | | |
|---|---|---|---|---|---|---|---|---|
| | 1 | 2 | 3 | 4 | 5 | 6 | 7 | 8 |
| Composition of the culture medium (in millimeters) | | | | | | | | |
| Pretreated whey | 75 | 73½ | 69½ | 69½ | 46 | 35 | 23 | — |
| Steamed skimmilk | — | — | 4 | — | 4 | 4 | 4 | 75 |
| 50% aqueous phosphate solution 1) | — | 1½ | 1½ | 1½ | 1½ | 1½ | 1½ | — |
| 4% w/v aqueous solution of sodium caseinate | — | — | — | 4 | — | — | — | — |
| Water | — | — | — | — | 23 | 35 | 46 | — |
| Activity of starter | | | | | | | | |
| Wi in L-milk | 32 | 41 | 44 | 42 | 44 | 39 | 38 | 44 |
| Wi in H-milk | 37 | 51 | 60 | 54 | 57 | 55 | 52 | 60 |
| Fr8 in L-milk | 25½ | 33 | 43 | 37 | 40 | 35 | 33 | 49 |
| Fr8 in H-milk | 33 | 51 | 57 | 53 | 56 | 53 | 49 | 61 |

1) 100 milliliters of this liquid contain: 28.3 g $Na_2HPO_4.2H_2O$ and 21.6 g $KH_2PO_4$ and after diluting (1 : 50 in the culture medium) the pH was 6.8.

EXAMPLE II

A starter was prepared on a technical scale. A mixture of first and second whey drainages, from which the majority of the protein had been removed after heating to 90° C and acidifying to a pH of 4.6, by centrifuging in a sludge centrifuge, was used. A quantity of 2300 liters of this whey was brought to a temperature of between 90° C and 95° C, pumped into a starter incubatively TGV-agar and ⅓% Wacca-agar [Th. Galesloot, F. Hassing and J. Stadhouders, NMZT 15 (1961) 127](using a 3 days' incubation at 25° C). The results are given in Table C. The activity of the starter was good, whilst in the freshly-made and in the concentrated starters there was an approximately equal ratio between the number of aroma-bacteria (betacocci) and the total number.

TABLE C

| Wi starter | Total number of germs (T) (× $10^7$ per ml) | Total number of betacocci (B) (× $10^6$ per ml) | Ratio B : T | Activity ° N in | |
|---|---|---|---|---|---|
| | | | | L-milk | H-milk |
| As a concentrate, but 40 times diluted after 1 day at −40° C | 121 | not determined | not determined | 56 | 57 |
| after 5 days at −40° C | 131 | 33 | 0,025 | not determined | not determined |

TABLE C-continued

| Wi starter | Total number of germs (T) ($\times 10^7$ per ml) | Total number of betacocci (B) ($\times 10^6$ per ml) | Ratio B : T | Activity ° N in | |
|---|---|---|---|---|---|
| | | | | L-milk | H-milk |
| As freshly-made starter | 54 | 15 | 0,028 | 66 | 61 |

EXAMPLE III

Figure 3:
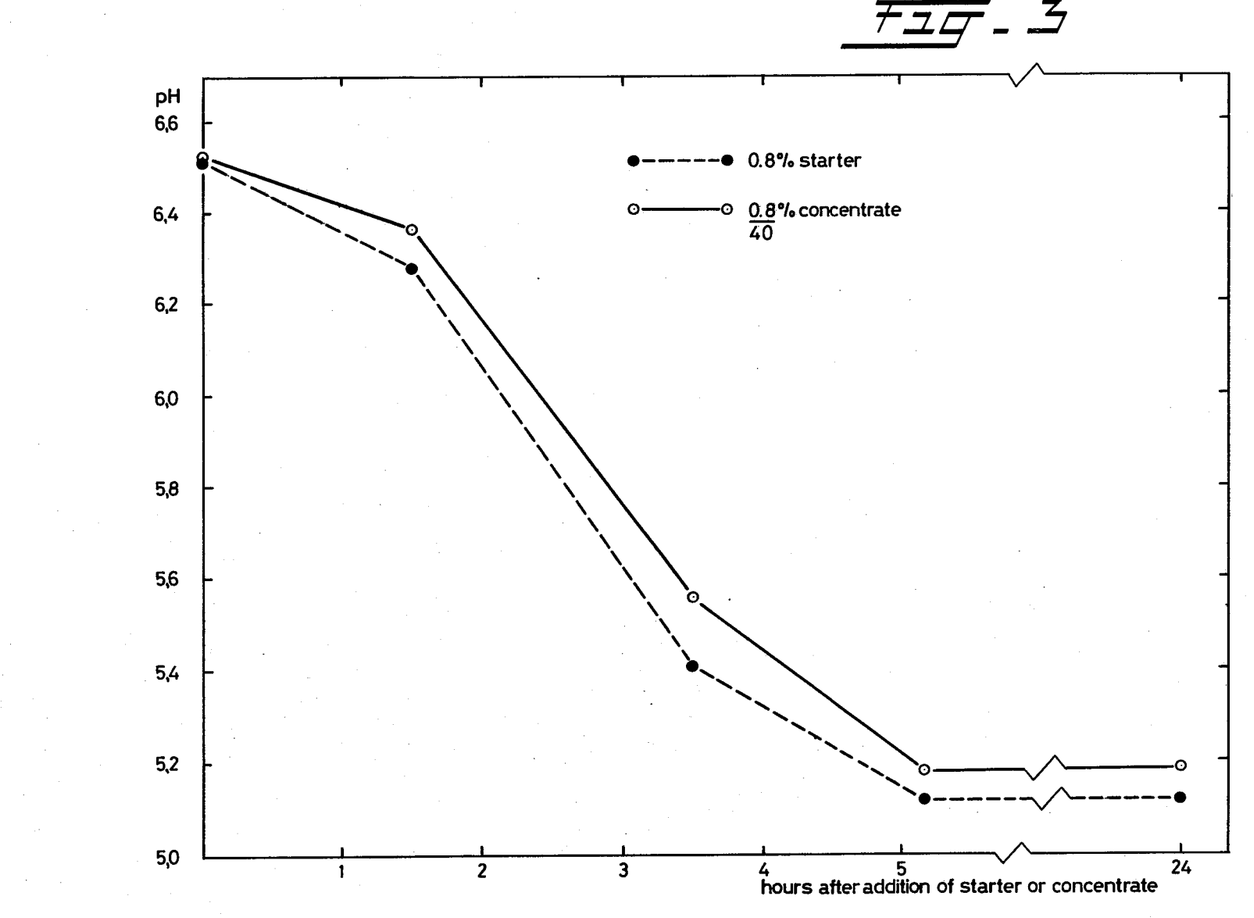

Five liters of a mixture of first and second whey drainings from cheese-making were steamed for 15 minutes and then centrifuged for 10 minutes at 10.000 × g to remove the precipitated protein. Into this pasteurized whey, 5% steamed skimmilk and 2% of a solution of 50% phosphate (made as in Example I) were introduced. Thereafter, this mixture was inoculated with 0.5% Wi starter and incubated at 20° C for 18 hours. Subsequently, and as in Example I, this starter was neutralized and clarified with 0.1% sodium citrate and subsequently the bacteria were removed by centrifuging for 10 minutes at 10.000 × g. The sediment was suspended into a part of the upper liquid to a total volume of 1/40 the of the original startervolume. This concentrate was used for making cheese from the same lot of milk and according to the same method as was cheese also made with the freshly prepared Wi starter of which 0.8 percent by volume was added to the milk. A corresponding quantity of 0.02% by volume of the concentrate was used. The progress of the lowering of the pH in the cheese, prepared with the starter concentrate, and in the cheese prepared with freshly made starter, is given in the accompanying FIG. 3. After 6 weeks, the cheese obtained were used to determine the $CO_2$ content. This was substantially the same (0.72 and 0.76 mg/g), whilst the organoleptic appreciation (taste and section) showed no differences.

EXAMPLE IV

A part of the frozen starter concentrate used in Example II was employed to cultivate cream for butter manufacture. In the preparation, no difficulties were encountered and the quality of the butter was normal.

EXAMPLE V

Another part of the frozen starter concentrate used in Example II was employed to prepare a bulk starter. The cheese-making process went forward absolutely normal and the cheese showed no deviations.

EXAMPLE VI

In the same whey as used in Example II, which was pasteurized after addition of the phosphate mixture to the same concentration as there mentioned, soy protein solution was added in place of skimmilk, the former having been heated for 10 minutes at 75° C before introduction as a 5% aqueous dispersion. The concentration of the soy protein, achieved after mixing with the culture medium was 0.25 and 0.50% by weight. Following cooling to 20° C, it was inoculated with 1% of one of the starters Wi or Fr8. After 18 hours incubation at 20° C, the activity of the starter was determined in accordance with the method of Example I. The results are given in Table D. It was found, also, with a substitution of soy protein for milk protein in the culture medium a starter was obtained, the activity of which was substantially the same as the activity of a skimmilk cultivated starter.

Table D

| Culture medium | Activity of the starter(° N) in | | | |
|---|---|---|---|---|
| | L-milk | | H-milk | |
| | Wi | Fr8 | Wi | Fr8 |
| Skimmilk | 64 | 47 | 67 | 64 |
| Whey + 1% (w/v) phosphate mixture + 0.25% (w/v) of soy protein | 58 | 34 | 61 | 57 |
| Whey + 1% (w/v) phosphate mixture + 0.50% of soy protein | 58 | 35 | 61 | 57 |

What we claim is:

1. A method of producing a composition for use as an inoculant material in the preparation of starters and fermented milk products, comprising (a) cultivating a culture of at least one strain of milk sugar fermenting bacteria in a culture medium consisting essentially of (1) undemineralized whey, (2) an aqueous dispersion of added non-whey protein selected from the group consisting of soya protein and milk casein in such an amount that the culture medium contains about 0.1 to 0.5 weight percent non-whey protein, and (3) a buffer mixture, said culture medium being prepared by separately pasteurizing said whey, said aqueous dispersion of non-whey protein and said buffer and mixing together the resultant pasteurized whey, aqueous dispersion of non-whey protein and buffer, (b) centrifuging the culture medium after said cultivating to concentrate more than 90% of the bacteria into a volume of about 2% of that of the culture medium prior to centrifuging and (c) freeze drying the bacteria concentrate to produce a composition which can be added directly to milk.

2. The method of claim 1 in which said culture medium is formed by mixing said whey said aqueous dispersion of non-whey protein, and said buffer mixture at a temperature not exceeding 65° C.

3. The method of claim 1 in which said whey comprises whey heated to a temperature of between 85° C. and 100° C. for a period of from 10 to 30 minutes.

4. The method of claim 3 in which said whey is clarified in a centrifuge after heating.

5. The method of claim 1 in which skim milk is used as said aqueous dispersion of non-whey protein.

6. The method of claim 5 in which from 5 to 10 percent of said skim milk is present in said culture medium.

7. The method of claim 1 in which said whey is supplemented with an assimilable carbohydrate.

8. The method of claim 7 in which said assimilable carbohydrate is a sugar.

9. The method of claim 1 in which said buffer mixture comprises a mixture of equi-molar quantities of disodiumhydrogen phosphate and potassium-dihydrogen phosphate.

10. In a method of preparing cheese in which milk is coagulated by adding rennin and a starter, the coagulated milk is cut into small pieces, the resulting mixture is gently stirred and, if necessary, heated to promote exudation of whey, the whey is drained off, and the curd is collected and shaped in a mold, the improvement comprising using as said starter the composition produced by the method of claim 1.

11. In a method of preparing fermented milk products in which milk is innoculated with a starter comprising a culture of microorganisms and the temperature of the inoculated milk is adjusted to obtain the necessary growth of the microorganisms, the improvement comprising using as said starter the composition produced by the method of claim 1.

12. The method of claim 1 in which said culture medium contains about 0.13 to 0.26 weight percent non-whey protein.

13. The method of claim 1 in which said whey comprises an aqueous solution of rennet-whey solids.

14. The method of claim 1 in which said whey comprises an aqueous dispersion of whey powder.

* * * * *